United States Patent
He et al.

(10) Patent No.: US 11,353,531 B2
(45) Date of Patent: Jun. 7, 2022

(54) METHOD FOR MEASURING RELAXATION TIME OF ULTRASHORT ECHO TIME MAGNETIC RESONANCE FINGERPRINTING

(71) Applicant: ZHEJIANG UNIVERSITY, Hangzhou (CN)

(72) Inventors: Hongjian He, Hangzhou (CN); Qing Li, Hangzhou (CN); Huihui Ye, Hangzhou (CN); Xiaozhi Cao, Hangzhou (CN); Jianhui Zhong, Hangzhou (CN); Qiuping Ding, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 0 days.

(21) Appl. No.: 17/263,549

(22) PCT Filed: May 9, 2020

(86) PCT No.: PCT/CN2020/089424
§ 371 (c)(1),
(2) Date: Jan. 27, 2021

(87) PCT Pub. No.: WO2020/228641
PCT Pub. Date: Nov. 19, 2020

(65) Prior Publication Data
US 2022/0057463 A1    Feb. 24, 2022

(30) Foreign Application Priority Data

May 10, 2019  (CN) .......................... 201910388149.4

(51) Int. Cl.
*G01R 33/50* (2006.01)
*G01R 33/48* (2006.01)
(Continued)

(52) U.S. Cl.
CPC .............. *G01R 33/50* (2013.01); *A61B 5/055* (2013.01); *A61B 5/4504* (2013.01); *G01R 33/4816* (2013.01); *G01R 33/4818* (2013.01)

(58) Field of Classification Search
CPC .. A61B 5/4504; A61B 5/055; G01R 33/4816; G01R 33/4818; G01R 33/50
See application file for complete search history.

(56) References Cited

U.S. PATENT DOCUMENTS

2015/0301141 A1* 10/2015 Griswold ........... G01R 33/5608
                                                              324/309
2018/0292483 A1    10/2018 Gulani et al.
(Continued)

FOREIGN PATENT DOCUMENTS

CN    105869192 A    8/2016
CN    107194354 A    9/2017
(Continued)

OTHER PUBLICATIONS

International Search Report (PCT/CN2020/089424); dated Jul. 29, 2020.
"Robust Sliding-Window Reconstruction for Accelerating the Acquisition of MR Fingerprinting" (Nov. 7, 2016) [Xiaozhi Cao et al.].
"Research progress on magnetic resonance with ultrashort echo time sequence" (Jan. 31, 2019) [Li Sha et al.].
(Continued)

Primary Examiner — Gregory H Curran
(74) Attorney, Agent, or Firm — W&G Law Group

(57) ABSTRACT

The present disclosure discloses a method for measuring relaxation time of ultrashort echo time magnetic resonance fingerprinting. In the method, semi-pulse excitation and semi-projection readout are adopted to shorten echo time (TE) to achieve acquisition of an ultrashort T2 time signal; and image acquisition and reconstruction are based on magnetic resonance fingerprint imaging technology. A TE change mode of sinusoidal fluctuation is introduced, so that distinguishing capability of a magnetic resonance fingerprint signal to short T2 and ultrashort T2 tissues is improved, and multi-parameter quantitative imaging of the short T2 and (Continued)

ultrashort T2 tissues and long T2 tissues is realized. Non-uniformity of a magnetic field is modulated into phase information of the fingerprint signal through the TE of the sinusoidal fluctuation; a B0 graph is directly reconstructed according to an amplitude-modulated signal demodulation principle; and the phase change caused by a B0 field is compensated in the fingerprint signal.

4 Claims, 8 Drawing Sheets

(51) Int. Cl.
  *A61B 5/00* (2006.01)
  *A61B 5/055* (2006.01)

(56) References Cited

U.S. PATENT DOCUMENTS

2019/0137585 A1* 5/2019 Bornert .............. G01R 33/4816
2020/0241096 A1* 7/2020 Bustin ................ G01R 33/4818

FOREIGN PATENT DOCUMENTS

| CN | 109073720 A | 12/2018 |
| CN | 110133553 A | 8/2019 |

* cited by examiner (a) Digital water film

- Muscle
- Achilles tendon
- Bone free water
- Total bone water
- Air 32
100 pixels (b) Tissue parameters

| | $T_1$ (ms) | $T_2$ (ms) | $T_2^*$ (ms) | PD | SNR |
|---|---|---|---|---|---|
| Muscle | 1400 | 32 | 114 | 1 | 28 |
| Achilles tendon | 621 | 3 | 9.9 | 0.8 | 20 |
| Total bone water | 246 | 1.2 | 1.7 | 0.7 | 14 |
| Bone free water | 524 | 3.5 | 7.6 | 0.3 | 7 |

List of quantitative results of UTE-MFR in the region of interest

| (ms) | #1 | #2 | #3 | #4 | #5 | #6 |
|---|---|---|---|---|---|---|
| $T_1$ | 163±10 | 164±8 | 158±9 | 164±15 | 559±13 | 446±13 |
| $T_2$ | 0.88±0.14 | 0.84±0.11 | 1.13±0.18 | 1.52±1.36 | 56±5 | 40±3 |
| (ms) | #7 | #8 | #9 | #10 | #11 | #12 (oil) |
| $T_1$ | 430±11 | 487±16 | 676±17 | 397±12 | 759±19 | 335±7 |
| $T_2$ | 42±3 | 45±3 | 62±2 | 37±3 | 85±7 | 122±11 |

METHOD FOR MEASURING RELAXATION TIME OF ULTRASHORT ECHO TIME MAGNETIC RESONANCE FINGERPRINTING

TECHNICAL FIELD

The present disclosure relates to the technical field of information processing, and in particular, to a method for measuring relaxation time of ultrashort echo time magnetic resonance fingerprinting.

BACKGROUND

The magnetic resonance technology provides an abundant contrast in soft tissue imaging. However, the traditional magnetic resonance technology can hardly detect the bone, Achilles tendon, meniscus and myelin sheath wall with short T2 or even ultrashort T2 (about 1-10 ms). The ultrashort echo technology and zero echo imaging technology have been widely used in the imaging of these tissues by shortening the echo time. Because the scanning time of single-point technology and multi-point technology is too long, it is rarely used in the research of subjects. In order to improve the sampling efficiency in k-space, the readout track with the center outward, including a semi-projection radial track and a spiral track, is used in signal acquisition. In the part of signal excitation, a half pulse excitation method is used in 2D imaging, while a hard pulse excitation method is used in 3D imaging.

The quantitative ultrashort echo technology has been applied to study a large number of bone and joint diseases, including articular cartilage degeneration, meniscus tear, age-related compact bone substance degeneration and osteoporosis. Compact bone substance water content is regarded as a new indicator of the quality of a compact bone substance. Quantitative calculation of a compact bone substance water content requires measuring T1 and T2* of a bone tissue, but it takes up to 1 hour to measure T1 and T2* of the bone tissue. In order to shorten the scanning time, Abbasi-Rad et al. used a method of measuring T1 with double repetition time combined with priori T2* information, but this method obviously ignored the difference of T2* between healthy volunteers and patients.

UTE and ZTE technologies are not only applied to the diagnosis of skeletal muscle diseases in a magneticresonance system, but also can provide pseudo-CT (pCT) images for positron emission tomography (PET) attenuation correction for a PET/MRI system. In order to enhance the signal of a bone tissue and suppress the signal of a long T2 tissue in background, a long T2 suppression pulse can be used as a signal excitation pulse or a short T2 selection pulse of double inversion recovery, or two images with different echo times can be used to make a difference in image reconstruction. Wiesinger et al. reconstructed pCT images from proton density images acquired from a ZTE sequence through an image segmentation method. Because soft tissues, bones and cavities have different relaxation times and proton densities, simultaneously quantifying multi-tissue parameters can also be used to enhance a bone tissue structure.

Magnetic resonance fingerprinting (MRF) technology can realize simultaneous quantitative imaging of multiple parameters, and this method can be applied to quantitative analysis of a bone tissue. The MRF technology models different quantitative indexes of tissues, including T1, T2, T2* and proton density (PD), into the change of a MRF signal curve by changing the parameters such as a signal flip angle (FA), a repetition time TR and an echo time TE. In addition, the MRF technology has shown clinical potential in brain and abdominal scanning. However, there are still challenges in quantifying ultrashort T2 tissues for the existing MRF technology.

Firstly, because the shortest echo time of the traditional MRF technology is several milliseconds, it is difficult for MRF to detect ultrashort T2 tissue signals.

Secondly, a tissue with ultrashort T2 usually has a low proton density, which makes the whole signal intensity low, thus reducing the accuracy of MRF dictionary recognition.

Thirdly, in order to avoid the influence of T2* ambiguity on readout signals, it is necessary to limit the width of the readout window to 0.81T2 in 2D imaging, and the optimized sampling window width is only a few hundred microseconds for a compact bone substance.

Finally, compared with the spiral readout of the traditional MRF, each radial readout contains less data. In order to reduce the down-sampled artifacts at a single MRF time point, it is necessary to collect signals from multiple radial tracks at each MRF time point.

SUMMARY

The purpose of the present disclosure is to provide a method for measuring the relaxation time of ultrashort echo time magnetic resonance fingerprinting based on sinusoidal fluctuation echo time aiming at the defects of the prior art.

In order to achieve the above purpose, the present disclosure adopts the following technical solution:

A method for measuring relaxation time of ultrashort echo time magnetic resonance fingerprinting, including steps of:

S1, establishing design and implementation of an echo magnetic resonance fingerprint imaging sequence, including optimization of sinusoidal fluctuation echo time parameters;

S2, scanning a subject through a magnetic resonance scanner by utilizing the echo magnetic resonance fingerprint imaging sequence established in S1, so as to obtain original k-space data;

S3, reconstructing the original k-space data obtained in S2 into a series of down-sampled images;

S4, phases of the series of down-sampled images in S3 being results of the echo time TE of sinusoidal fluctuation modulated with non-uniformity of a B0 field:
Phase=2pi·$B_{off}$·($\alpha$ sin($\omega\tau$)+$\beta$)+n, where, $B_{off}$ is a frequency shift caused by field non-uniformity and chemical shift and has a unit of Hz, $\alpha$, $\beta$ and $\omega$ are sampling parameters of the TE, $\alpha=(TE_{max}-TE_{min})/2$, $\beta=(TE_{max}+TE_{min})/2$, $TE_{max}$ and $TE_{min}$ are respectively maximum TE and minimum TE; $\omega$ is a frequency of a sinusoidal wave; $\tau$ is a time vector $[1, 2, \ldots, F]^T$, and the time unit is a repetition time TR; n represents a noise term, and demodulation of $B_{off}$ is realized by multiplying a carrier sin($\omega\tau$) followed by low-pass filtering;

S5, moving-averaging a fingerprint signal by sliding window technology, and then performing amplitude demodulation on S4, that is, calculating $B_{off}$:

$$B_{off} = \frac{2}{2\pi \cdot \alpha \cdot mT}.$$

$\Sigma_0^{mT}$(S·dPhase) by multiplying by the carrier sin($\omega\tau$) followed by low-pass filtering;

in which, dPhase is a phase signal multiplied by sin($\omega\tau$) in S4, mT is a phase integral period, m is a number of cycles, π is PI, T=2π/ω, S is a matrix of F×F, an element contained is either 0 or 1, each row of S represents a window; if and only if the signal is in the window, a value of the element is 1, otherwise the value of the element is 0; and from the first row to the last row in the matrix S, the window moves from left to right;

S6, compensating $B_{off}$ calculated in S5 into the fingerprint signal processed by sliding window; then, reconstructing a multi-parameter quantitative graph from the collected fingerprint signal by a dictionary recognition method in the magnetic resonance fingerprint imaging technology; and S7, according to tissue relaxation time reconstructed in S6, looking up in a dictionary to obtain a corresponding longitudinal magnetization vector change curve, selecting an image with a highest contrast of a bone tissue as a bone enhancement image, which is recorded as Mz, and using Mz/T1 as output of the bone enhancement image, so as to suppress a long T1 tissue, where T1 is a quantitative result of the longitudinal relaxation time outputted in S6.

Furthermore, the optimization of parameters in S1 is implemented by selecting echo time parameters with the highest measurement accuracy by a MATLAB simulation method, and the echo time parameters includes the minimum echo time, the maximum echo time and a sinusoidal fluctuation period.

Furthermore, in S3, the original k-space data in S2 is reconstructed into the series of down-sampled images by a non-uniform fast Fourier transform reconstruction algorithm.

Furthermore, in S5, when a width of the sliding window is 4, S can be written as:

$$S = \begin{pmatrix} 1 & 1 & 1 & 1 & 0 & \dots & 0 & 0 \\ 0 & 1 & 1 & 1 & 1 & \dots & 0 & 0 \\ 0 & 0 & 1 & 1 & 1 & \dots & 0 & 0 \\ & & & \vdots & & & & \\ 0 & 0 & 0 & 0 & 0 & \dots & 1 & 1 \end{pmatrix}_{F \times F}.$$

Parameters in that method are defined as follow:

T1: longitudinal relaxation time, which refers to the time required for a longitudinal magnetization vector to recover from zero to 67% of the total signal strength;

T2: transverse relaxation time, which refers to the time required for a transverse magnetization vector to decay from 100% to 37%; according to a duration of the transverse relaxation time, tissues can be divided into ultrashort T2 tissues (T2≤1 ms), short T2 tissues (1 ms<T2≤10 ms) and long T2 tissues (10 ms<T2). The bone is a common ultrashort T2 tissue, and soft tissues such as muscles belong to long T2 tissues.

T2*: effective transverse relaxation time, which refers to the time required for a transverse magnetization vector to decay from 100% to 37% in presence of magnetic field non-uniformity;

T2': change of the transverse relaxation time caused by magnetic field non-uniformity, where 1/T2=1/T2*+1/T2';

PD: a proton density, which refers to a content of hydrogen protons;

B0: an intensity of a main magnetic field; a B0 graph usually only shows a difference of the magnetic field distribution relative to the main magnetic field;

FA: a flip angle, which refers to an angle by which an excitation pulse deviates the magnetization vector relative to the main magnetic field direction; when FA=90°, the magnetization vector is perpendicular to the main magnetic field direction.

TE: echo time, which refers to the time interval between a signal excitation center and an echo center. In UTE technology, TE refers to the time from the ending of an excitation pulse to the beginning of a readout gradient;

TR: repetition time, which refers to the time interval between two adjacent excitations of a sequence.

By adopting the technical solution of the present disclosure, the present disclosure has the following beneficial effects: compared with the prior art, firstly, the ultrashort echo magnetic resonance fingerprint imaging technology is adopted to realize T1 and T2 relaxation of short T2 and ultrashort T2 tissues, and the time are measured quantitatively at the same time; and by proposing a coding mode of sinusoidal fluctuation echo time magnetic resonance fingerprint signals, the distinguishing ability and quantitative accuracy of magnetic resonance fingerprint signals on short T2 and ultrashort T2 tissues are improved. The method base on amplitude modulation and demodulation proposed in that present disclosure realize the direct demodulation estimation of a B0 field without increasing extra dictionary calculation and reconstruction calculation. Finally, according to the generated longitudinal magnetization vector diagram, the present disclosure proposes a Mz/T1 method to suppress the long T2 signals and generate bone enhancement images at the same time.

DESCRIPTION OF EMBODIMENTS

The specific embodiment of the specific scheme of the present disclosure will be further explained with reference to the attached drawings.

Figure 1A:
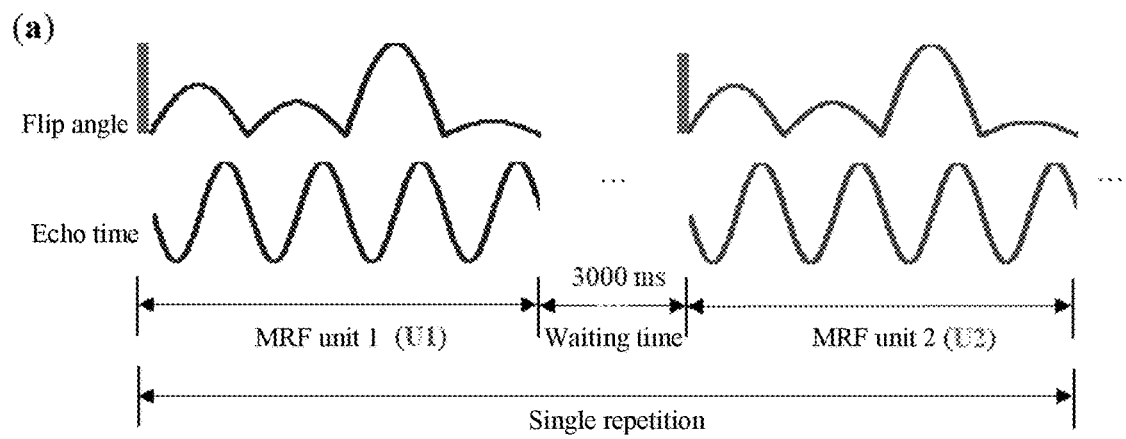
FIG. 1a is the coding mode of a flip angle (FA) and an echo time (TE) in a sequence scanning according to the present disclosure.
Figure 1B:
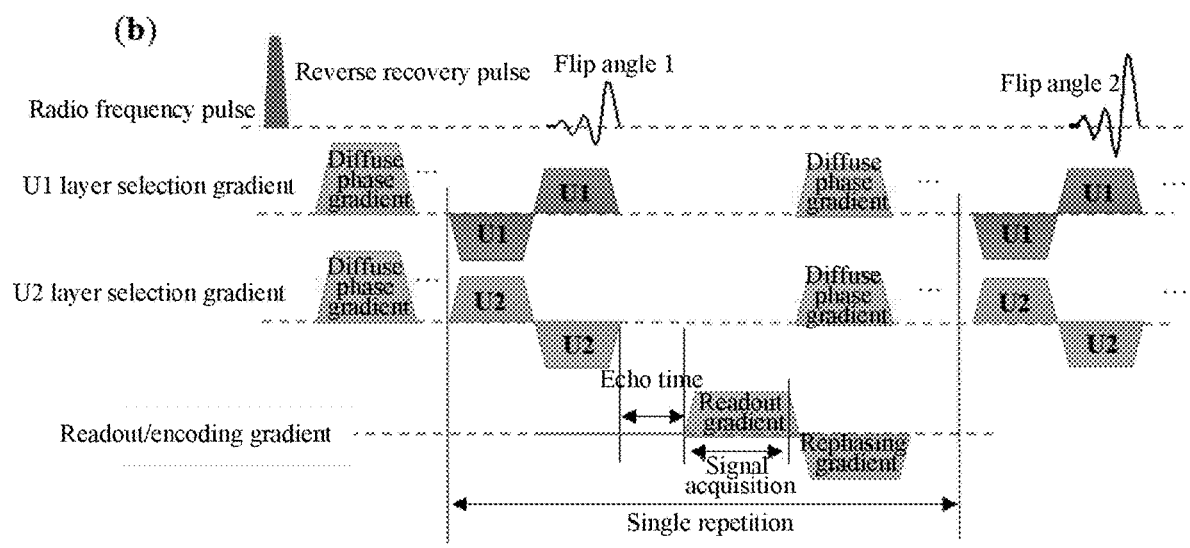
FIG. 1b is a schematic sequence diagram of an ultrashort echo magnetic resonance fingerprint imaging technology within an echo time (TR) of the present disclosure.

As shown in FIGS. 1a and 1b, they respectively show the encoding parameters for signals of magnetic resonance fingerprinting (MRF) and a schematic sequence diagram of two-dimensional ultrashort echo magnetic resonance fingerprinting (UTE-MRF) based on fast imaging with steady-state precession (FISP). In order to reduce the echo time, the half-pulse excitation technology is adopted. A sinc pulse with a pulse duration of 1.2 ms and a time bandwidth product of 6 is divided into two and a half pulses. The peak energy and truncated gradient trajectory of RF is reduced to 0 through a variable-rate selective excitation (VERSE) algorithm, and the generated half-pulse duration is 0.7 ms. Half-pulse is applied along with positive and negative bipolar gradient pulses to realize complete layer selection and improve the robustness of the layer selection gradient to an eddy current. One UTE-MRF unit contains 480 images with high downsampling, and the flip angle (FA) and echo time (TE) in the image sequence are continuously changing. A FA is composed of four groups of semi-periodic sinusoidal waves, in which the peak FA intensities are 32°, 22°, 60° and 10° respectively, and the minimum FA is 5°. The TE changes according to the sinusoidal waveform, in which the minimum TE is 0.05 ms, the maximum TE is 0.6 ms, and the fluctuation period of the TE is 120 (unit: TR). TR is fixed at 6 ms.

In order to shorten the echo time, a ramp sampling technology is adopted in UTE-MRF, with a readout window width of 0.79 ms, including: a gradient platform time of 0.64 ms and a ramp time of 0.15 ms, and a readout bandwidth of 1780 Hz/pixel. A waiting period of 3 s is set after the first UTE-MRF unit, in order to restore the proton to its initial state before the second MRF unit. When scanning repeatedly, a delay interval of 3 s is for the purpose of restoring the longitudinal magnetization vector. In order to maximize the signal-to-noise-ratio (SNR) and control the scanning time within 1 minute, the number of repetitions of the water film, ankle and brain tissue scanning is 5. For quantification of the compact bone substance of the lower leg, scanning is repeated once more, and the total scanning time is increased to 68 sin order to improve SNR. In order to increase the inconsistency between MRF images and reduce the influence of the eddy current on image quality, the radial readout track rotates at a small golden angle (23.62°). At the same time point with different repetition times of MRF, radial trajectories are evenly distributed on the unit circle.

In the existing research of the MRF technology, the change of the echo time is introduced to improve the sensitivity of MRF to T2*, which is used to distinguish the signals of water and fat. In the UTE-MRF technology, a TE mode with sinusoidal variation is used to improve the sensitivity of MRF to short or even ultrashort T2 tissues.

Figure 2:
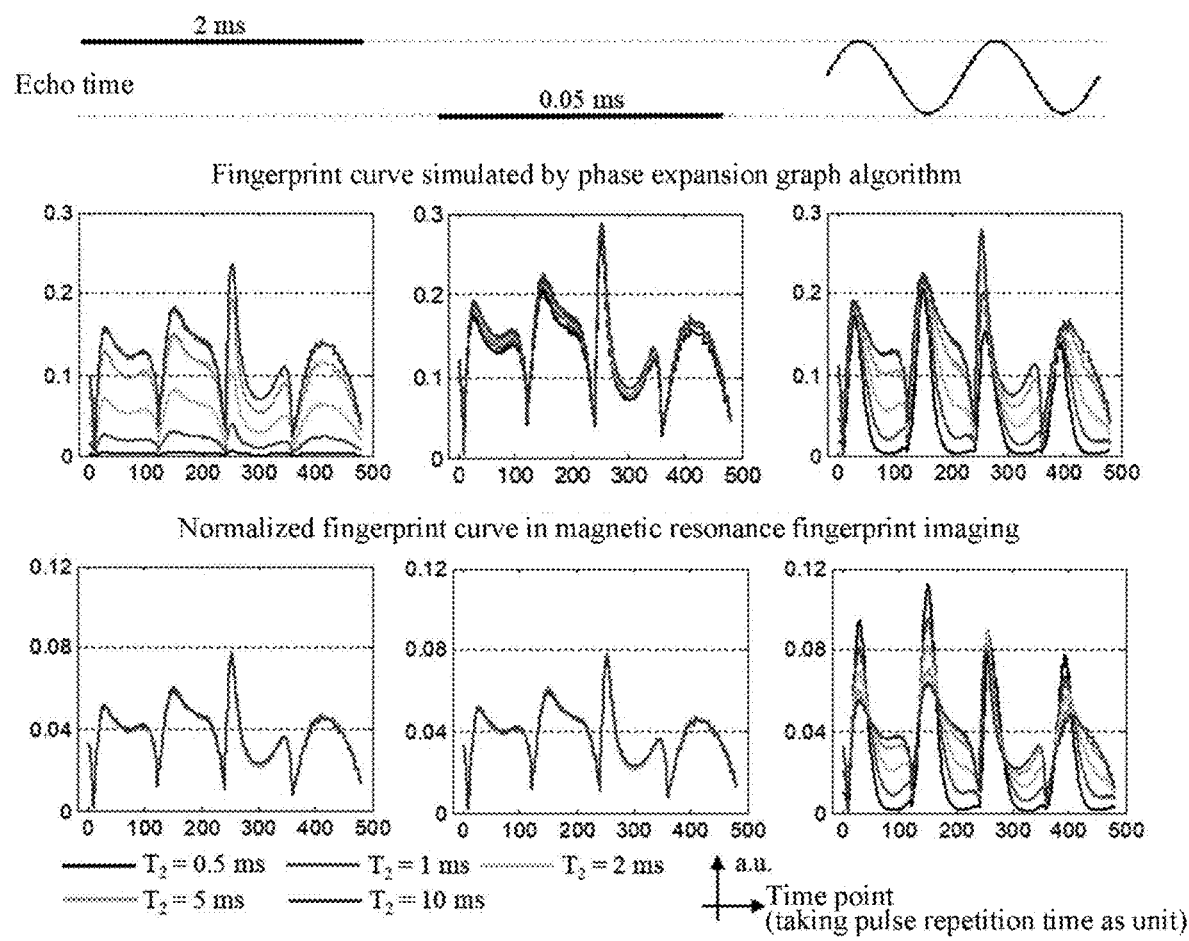
FIG. 2 is a schematic diagram showing the effect of the sinusoidal fluctuation echo time method of the present disclosure on improving the difference between signal curves.

As shown in FIG. 2, it shows the signal curves of six different organizations simulated by extended phase graph (EPG). For these organizations, T1=180 ms, T2=0.5, 1, 2, 5 and 10 ms, and the FA change pattern in FIG. 1(b) is adopted. When TE is constant (the first two columns of FIG. 2), it is difficult to distinguish the normalized signals of different relaxation time organizations, even when TE is minimized to 0.05 ms. However, in the sinusoidal TE mode (the minimum TE is 0.05 ms and the maximum TE is 2 ms), the signal curves of various tissues can be visually distinguished. However, when the magnetic field is uneven, the changing TE will introduce the phase varying with the time of TE and space position in the MRF image sequence.

In order to avoid the loss of phase information, the extra phase caused by non-uniformity of the magnetic field can be solved by: a) pre-scanning a B0 map and compensating the phase caused by B0; b) modeling the non-resonance effect in MRF dictionary.

However, the above methods need to increase the calculation amount in MRF dictionary calculation and recognition. According to the present disclosure, a dictionary free B0 estimation method is proposed through a sinusoidal TE change mode. The accumulated phase in the MRF image sequence is modulated by a non-uniform field $B_{off}$ and the TE of the sinusoidal fluctuation, and the modulated carrier is ($\alpha \sin(\omega\tau)+\beta$), $$\text{Phase}=2pi \cdot B_{off} \cdot (\alpha \sin(\omega\tau)+\beta)+n,$$

where, $B_{off}$ is the frequency shift caused by field non-uniformity and chemical shift, with the unit being Hz; $\alpha$, $\beta$ and $\omega$ are the sampling parameters of TE, $\alpha=(TE_{max}-TE_{min})/2$, $\beta=(TE_{max}+TE_{min})/2$, $TE_{max}$ and $TE_{min}$ are the maximum time and the minimum echo time respectively; $\omega$ is the frequency of a sinusoidal wave; $\tau$ is the time vector$[1, 2, \ldots, F]^T$, with the repetition time (TR) as the unit; n represents the noise term, and the demodulation of $B_{off}$ is realized by multiplying the carrier $\sin(\omega\tau)$ followed by low-pass filtering:

$$d\text{Phase}=(2\pi \cdot B_{off} (\alpha \sin(\omega\tau)+\beta)+n) \cdot \sin(\omega\tau).$$

dPhase is further written as:

$$dPhase = 2\pi \cdot B_{off} \cdot \alpha \cdot \left(\frac{1-\cos(2\omega\tau)}{2}\right) + (2\pi \cdot B_{off} \cdot \beta + n) \cdot \sin(\omega\tau).$$

In the above formula, $B_{off}$ is the frequency shift caused by field non-uniformity and chemical shift, with the unit being Hz; $\alpha$, $\beta$ and $\omega$ are the sampling parameters of TE, $\alpha=(TE_{max}-TE_{min})/2, \beta=(TE_{max}+TE_{min})/2$, $TE_{max}$ and $TE_{min}$ are the maximum time and the minimum echo time respectively; $\omega$ is the frequency of a sinusoidal wave; $\tau$ is the time vector$[1, 2, \ldots, F]^T$, with one repetition time (TR) as the time unit; n represents the noise term. The noise item in the above formula includes physiological noises, thermal noises and other noises related to a MRI system. However, since each image in aMRI image sequence is reconstructed from K-space data collected in one TR, most of the signals in the noise term n come from the down-sampled artifacts of the image. In order to reduce the phase noise caused by k-space down-sampling, the sliding window algorithm is applied to the above formula, and the phase image sequence is moving-averaged by multiplying the sliding window matrix at both the left and right sides of the equation dPhase=$(2\pi \cdot B_{off}(\alpha \sin(\omega\tau)+\beta)+n) \cdot \sin(\omega\tau)$:

$$S \cdot dPhase = 2\pi \cdot S \cdot B_{off} \cdot \alpha \cdot \left(\frac{1-\cos(2\omega\tau)}{2}\right) + S \cdot (2\pi \cdot B_{off} \cdot \beta + n) \cdot \sin(\omega\tau).$$

In the above formula, S is a matrix of F×F, and its elements are either 0 or 1. $B_{off}$ is the frequency shift caused by field non-uniformity and chemical shift, with the unit being Hz; α, β and ω are the sampling parameters of TE, $\alpha=(TE_{max}-TE_{min})/2$, $\beta=(TE_{max}+TE_{min})/2$, $TE_{max}$ and $TE_{min}$ are the maximum time and the minimum echo time respectively; ω is the frequency of a sinusoidal wave; τ is the time vector$[1, 2, \ldots, F]^T$, with one repetition time (TR) as the time unit; n represents the noise term. Each row of S represents a window; if and only if the signal is in the window, the value of the element is 1, otherwise the value is 0; from the first row to the last row in the matrix S, the window moves from left to right. When a width of the sliding window is 4, S can be written as:

$$S = \begin{pmatrix} 1 & 1 & 1 & 1 & 0 & \ldots & 0 & 0 \\ 0 & 1 & 1 & 1 & 1 & \ldots & 0 & 0 \\ 0 & 0 & 1 & 1 & 1 & \ldots & 0 & 0 \\ & & & \vdots & & & & \\ 0 & 0 & 0 & 0 & 0 & \ldots & 1 & 1 \end{pmatrix}_{F \times F}.$$

The influence of the phase image noise term n processed by sliding window is almost negligible, so it is considered that the noise term after sliding window is 0. The integral of time in the change period of integral multiples of the TE can be regarded as a low-pass filter, so that the phase terms with $\cos(2\omega\tau)$ and $\sin(\omega\tau)$ as the carriers will be filtered out, and thus $B_{off}$ is derived as:

$$B_{off} = \frac{2}{2\pi \cdot \alpha \cdot mT} \cdot \sum_0^{mT}(S \cdot dPhase),$$

where, mT is the phase integration period, m is the number of periods, $T=2\pi/\omega$, ω is the sinusoidal wave frequency, $\alpha=(TE_{max}-TE_{min})/2$, $\beta=(TE_{max}+TE_{min})/2$, $TE_{max}$ and $TE_{min}$ are the maximum and minimum echo times respectively.

The MRF dictionary is calculated by the extended phase graph (EPG) method according to the FA pattern and the TE variation pattern of the sine (the minimum TE=0.05 ms, and the maximum TE=[0.05:0.05:1.0] ms) in FIG. 1(b). In this example, the TE period is set to 120 TRs. The longitudinal recovery time T1 of the dictionary ranges from 10 ms to 3000 ms, specifically: [10: 10: 400, 400: 20: 2000, 2000: 40: 3000] ms. The transverse relaxation time T2 ranges from 0.1 ms to 300 ms, specifically: [0.1: 0.1: 5,5: 5: 150,150: 10: 300] ms Considering the partial recovery effect of the longitudinal magnetization vector, a two-step dictionary design method is adopted, and the areas covered by all curves in the dictionary are normalized to 1.

The quantitative graphs of multi-parameters T1, T2, PD and B0 are reconstructed by the following four steps. In Step 1, multi-channel images are reconstructed from multi-channel k space by using a non-uniform fast Fourier transform (NUFFT) algorithm, and then a single image is synthesized by using an adaptive coil superposition method. Then, the images from positive and negative polarity gradient excitation are directly added in complex numbers, and an image of a complete selected layer is obtained. In Step 2, by using the formula $$B_{off} = \frac{2}{2pi \cdot \alpha \cdot mT} \cdot \sum_0^{mT}(S \cdot dPhase),$$

a B0 image is estimated from the phase part of the image in Step 1. In order to reduce the interference of down-sampling aliasing and reduce the loss of a MRF signal specificity, the sliding window width is set to be 20. At the same time, in order to avoid the influence of the phase inversion caused by IR, phase diagrams of only 240 to 480 TRs (i.e., two TE change periods) are used. In Step 3, in order to remove the phase interference caused by the field non-uniformity, the field non-uniformity estimated in Step 2 is compensated into plural MRF image sequences. In Step 4: the image sequence of MRF is normalized and the dictionary curve most similar to the scanning signal is found out by a method of point multiplication with dictionary curve. Compared with the bone marrow, the radial downsampling artifact has more interference on the recognition of a compact bone substance because of its low proton density and ultrashort T2 value. Therefore, before bone signal recognition, the bone marrow components in the signal are estimated and removed by partial volume dictionary recognition, and then a multi-parameter quantitative graph is reconstructed by MRF dictionary recognition.

In order to introduce the T1 weighting into the signal, an adiabatic inversion pulse is used in MRF, which makes the image signal of the MRF show a soft tissue inhibition effect when the long T2 tissue inversion returns to zero point. Based on this characteristic, this chapter proposes a bone enhanced image reconstruction method. Although the bone tissue has ultrashort T2, which causes the signal attenuation in the transverse plane to be very fast, the short T1 property makes it recover faster in the longitudinal plane than the long T2 tissue, so the bone tissue shows a high signal in the longitudinal magnetization vector diagram. Because the MRF technology can quantify T1 and T2 relaxation times of tissues, transverse and longitudinal magnetization vector diagrams at any time in MRF scanning can be obtained by reverse dictionary lookup. Finally, the image in which the ultrashort T2 bone signal is enhanced in the longitudinal magnetization vector image is selected as the skull enhancement image.

Figures 3A, 3B:
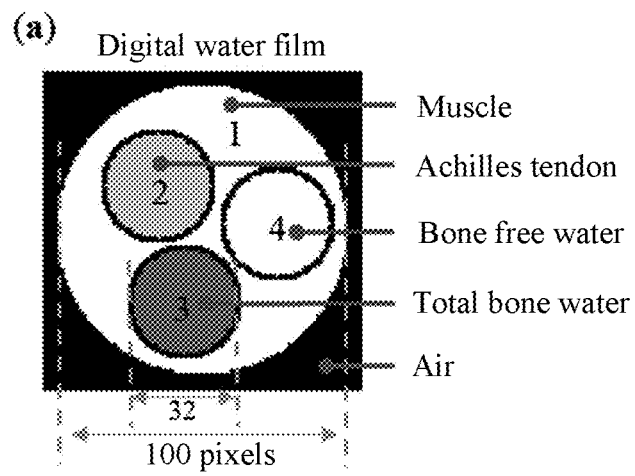
FIG. 3a is a schematic diagram of a simulated water film structure of the present disclosure.
FIG. 3b is a list of various tissue relaxation parameters of the simulated water film of the present disclosure.

In order to study the influence of the sinusoidal TE sampling mode on the accuracy of tissue quantification, simulation experiments are carried out on the digital water film (110×110) as shown in FIGS. 3a and 3b. The digital water film contains all water signals of the muscle, Achilles tendon and bone, and free water signals of the bone. The black area in the water film represents air. In FIG. 3(b), the parametric characteristics of tissues are listed. The ideal MRF image sequence comes from the transverse magnetization vector calculated by the EPG algorithm. Although the TE change improves the specificity of MRF for short T2 or even ultrashort T2 tissue, T2* weighting caused by TE change is also introduced into the image. Because the T2 effect of the tissue has been simulated into the MRF signal curve by EPG, the effect of T2* is realized by multiplying the ideal MRF signal curve by an additional T2 attenuation term, because T2* is the comprehensive effect of T2 and T2': exp(TE/T2*)=exp(TE/T2+TE/T2'). The ideal value of T2 is shown in FIG. 3(b), which makes T2* of the muscle 25 ms, T2* of the Achilles tendon 2.3 ms, T2* of the total bone water 0.7 ms and T2* of the free bone water 2.4 ms.

Figure 4A:
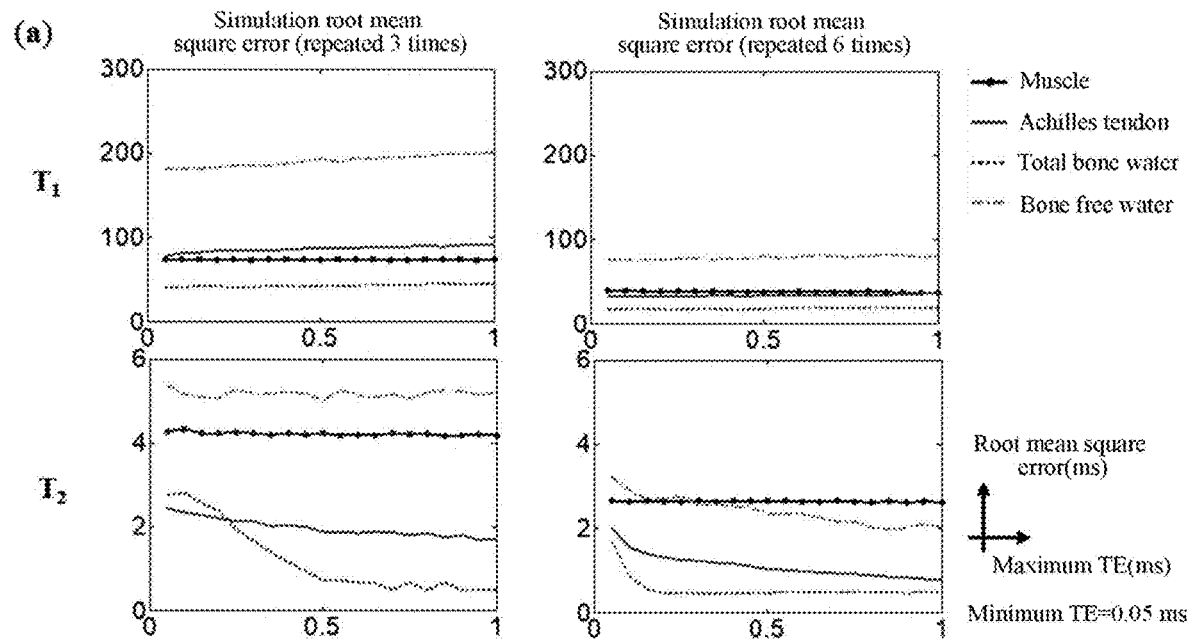
FIG. 4a shows the influence of different echo time change ranges on the measurement of relaxation time of tissues T1 and T2, and the images in left and right columns are the results of repeated scanning of the sequence in FIG. 1a for three times and six times respectively.
Figure 4B:
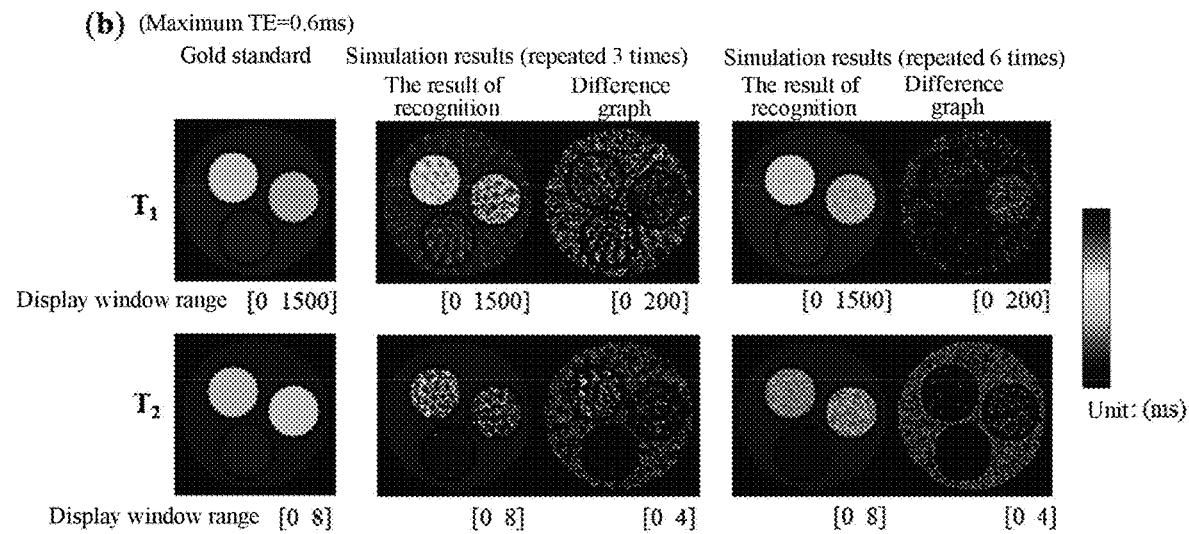
FIG. 4b is a comparison diagram and a residual diagram between simulation results and theoretical results in the case of a maximum TE=0.6 ms in FIG. 4a according to the present disclosure.

In the simulation experiment, the influence of a SNR difference of different tissues on quantification is also considered. Complex Gaussian white noises with different noise intensities are added to the signal of MRF, so that the SNRs of different tissues are shown in FIG. 3(b). The MRF transverse magnetization vector with noise is transformed into the k space by the NUFFT algorithm, in which the radial sampling track of golden angle rotation and the corresponding density compensation function are needed. The minimum TE is fixed at 0.05 ms, and the maximum TE is increased from 0.05 ms to 1 ms with a step size of 0.05 ms. The quantitative multi-parameter graphs adopt the method introduced in the image reconstruction in the previous section. The root mean square error (RMSE) between the measured values of T1 and T2 and the ideal values of T1 and T2 was calculated as the result. The simulation results are shown in FIGS. 4a and 4b.

Figure 5:
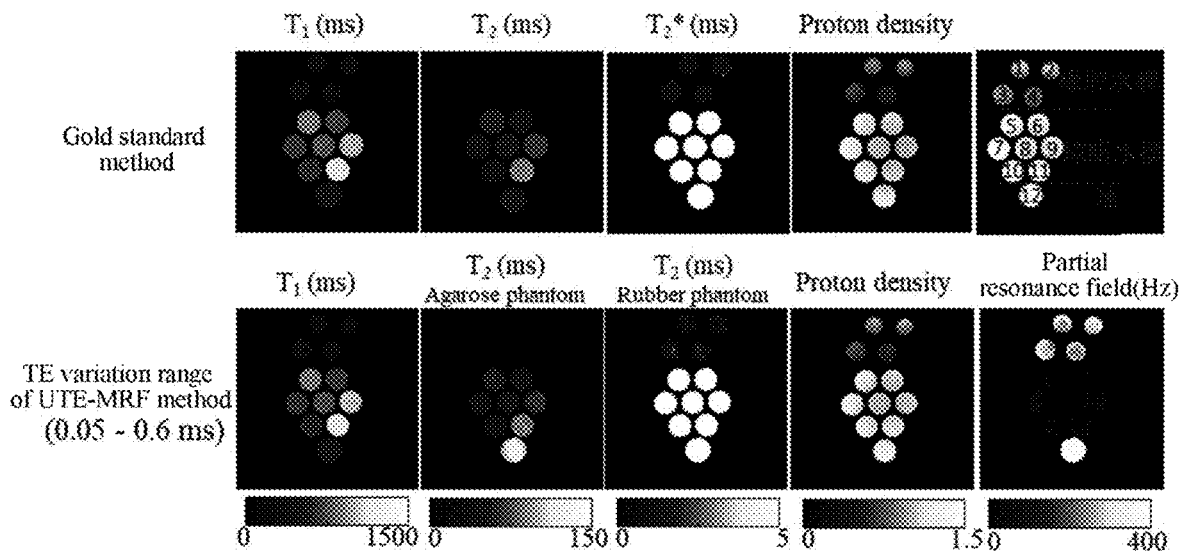
FIG. 5 is a comparison diagram of the measurement results of the UTE-MRF method of the water film of the present disclosure and the gold standard method.
Figure 6A:
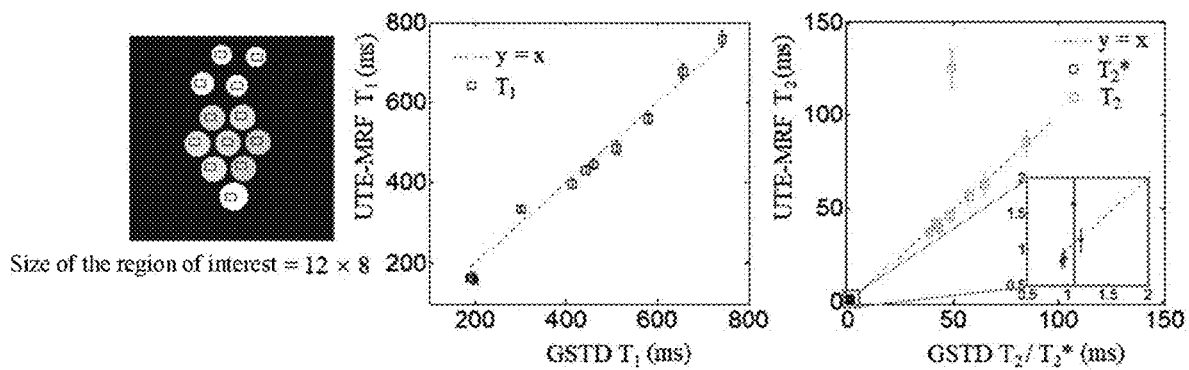
FIG. 6a is a result analysis diagram of FIG. 5 based on the region of interest according to the present disclosure.

The scanning subjects in the experiment are self-made an agar water membrane to simulate a soft tissue and a rubber sieve to simulate a ultrashort T2 tissue. The magnetic resonance signals are collected by a 20-channel head coil. The agar water membrane contains 7 test tubes, which are composed of MnCl2 agar gels with different concentrations, and is used to simulate the difference between T1 and T2 in tissues. There is also a test tube filled with vegetable oil (containing 94% soybean oil and 6% sunflower oil). The sample of this vegetable oil has a main resonance frequency, and the deviation between its central frequency and water is about 3.46 ppm. A gold standard T1 graph is acquired by an inversion recovery ultrashort echo time (IR-UTE) sequence, in which the TE time is 50, 100, 200, 400 and 800 ms, TR=3000 ms, TE=0.05 ms, the radial number=248. All the data collected by IR-UTE and UTE sequences are reconstructed by the algorithm of the MRF image reconstruction in Step 1. The T2 quantitative diagram of the gold standard is measured by a SE sequence, in which TE=25, 50, 75, 100 and 125 ms, TR=3000 ms, a reconstruction matrix=192×192, the resolution=1×1 mm2, and 6/8 of Fourier acquisition is adopted. The acquisition time of gold standard scanning is as follows: T1: 124 minutes, T2*: 74 minutes, and T2: 36 minutes. The experimental results of the water film are shown in FIGS. 5, 6a and 6b.

Figures 6B, 7:
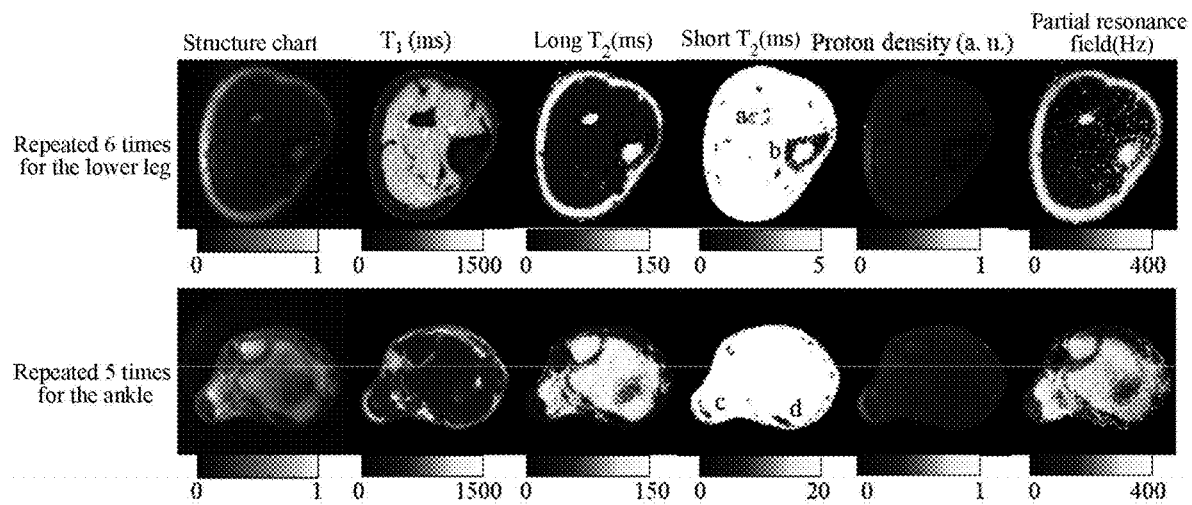
FIG. 6b is a list of detailed measurement parameters of the region of interest in FIG. 6a according to the present disclosure.
FIG. 7 is a schematic diagram of the experimental results of system scanning of the subject's skeletal muscle according to the present disclosure.
Figure 8:
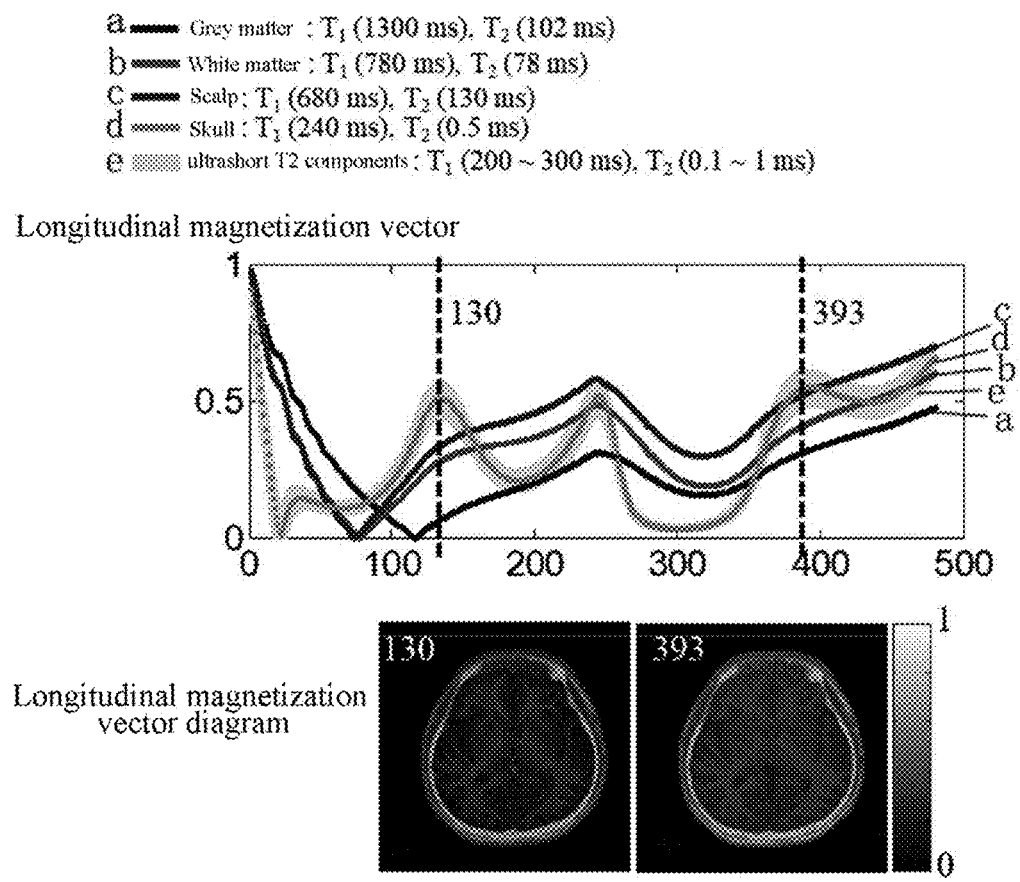
FIG. 8 shows the change of longitudinal magnetization vectors of different tissues according to the present disclosure.
Figure 9:
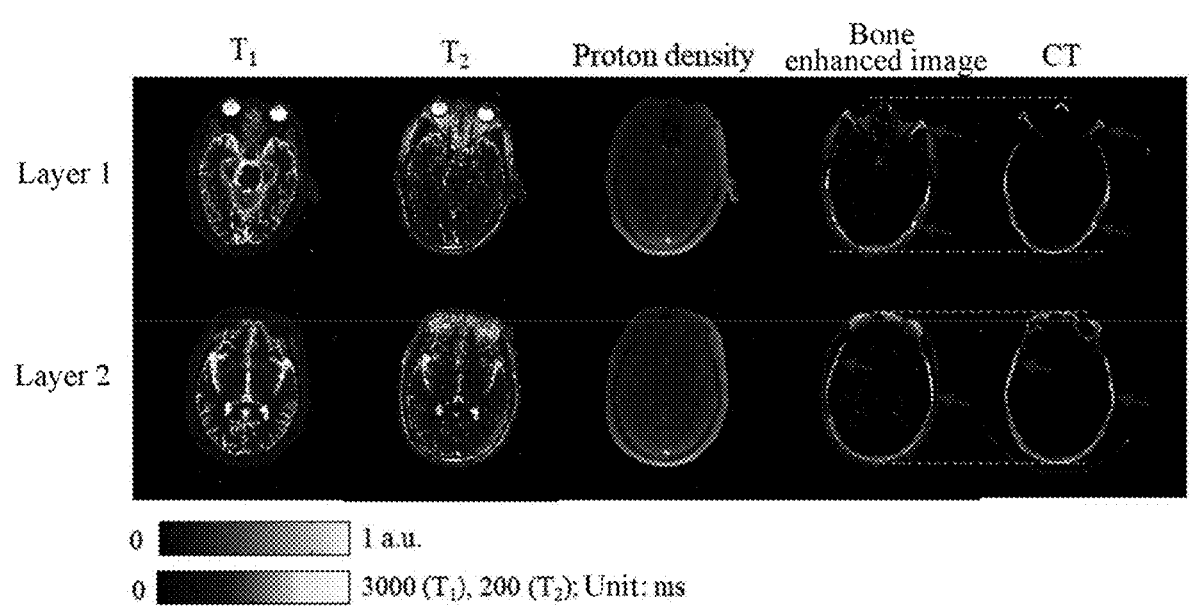
FIG. 9 is a schematic diagram showing the comparison between the experimental results of scanning of the subject's brain and CT images according to the present disclosure.

For imaging of the calf and Achilles tendon, 15-channel knee coils are used for signal acquisition, and the results are shown in FIG. 7. For brain scanning of patients with facial neuroma, the scanning coil adopts a 64-channel head coil. Considering the safety of scanning, the amplitude of the FA sequence is reduced by half. FIG. 8 shows the longitudinal magnetization vector change curve simulated based on the relaxation time of a brain tissue, and the longitudinal magnetization vector diagram when the number of frames is 130 and 393. FIG. 9 shows a comparison between the reconstructed bone enhancement image of the patient and the CT image of the patient, in which the detailed parameters of CT acquisition are: a tube voltage=80 kV, a tube current=365 mA, DLP=97.9 mGy·cm, an average radiation dose=0.34 mSv, a slice thickness=1.0 mm, and a resolution=0.5×0.5 mm$^2$). CT data are collected from a Philips iCT instrument (Philips Healthcare, The Netherlands) in a local hospital through preoperative navigation. The 3D CT image is registered with the 2D MRI image by using the 3D rotation function of a RadiAntDicom Viewer (Medixant Co., Poland).

The imaging layer thickness of the water film is 6 mm, and the scanning layer thickness of a human body is 7 mm. In order to improve the image quality of a skull enhanced image, the echo time during brain scanning keeps the minimum TE value (0.05 ms) unchanged. The multi-parameter quantitative result graph is reconstructed by MATLAB R2014a (The MathWorks, MA) on a Linux server (Core i7 Intel Xeon 2.8 GHz CPUs and 64 GB RAM). The reconstruction resolution of the water film, calf and Achilles tendon is 1.0×1.0 mm$^2$ (reconstruction matrix=240×240), and the resolution of the brain tissue is 0.75×0.75 mm$^2$ (the matrix size=256×256). All the above experiments are carried out on a Siemens Prisma scanner. Parameters in the embodiment are defined as follows:

T1: longitudinal relaxation time, which refers to the time required for a longitudinal magnetization vector to recover from zero to 67% of the total signal strength;

T2: transverse relaxation time, which refers to the time required for a transverse magnetization vector to decay from 100% to 37%; according to a duration of the transverse relaxation time, tissues can be divided into ultrashort T2 tissues (T2≤1 ms), short T2 tissues (1 ms<T2≤10 ms) and long T2 tissues (10 ms<T2). The bone is a common ultrashort T2 tissue, and soft tissues such as muscles belong to long T2 tissues.

T2*: effective transverse relaxation time, which refers to the time required for a transverse magnetization vector to decay from 100% to 37% in presence of magnetic field non-uniformity;

T2': change of the transverse relaxation time caused by magnetic field non-uniformity, where 1/T2=1/T2*+1/T2';

PD: a proton density, which refers to a content of hydrogen protons;

B0: an intensity of a main magnetic field; a B0 graph usually only shows a difference of the magnetic field distribution relative to the main magnetic field;

FA: a flip angle, which refers to an angle by which an excitation pulse deviates the magnetization vector relative to the main magnetic field direction; when FA=90°, the magnetization vector is perpendicular to the main magnetic field direction.

TE: echo time, which refers to the time interval between a signal excitation center and an echo center. In UTE technology, TE refers to the time from the ending of an excitation pulse to the beginning of a readout gradient;

TR: a repetition time, which refers to the time interval between two adjacent excitations of a sequence.

It should be noted that, the above description merely illustrates preferred embodiments of the present disclosure and the technical principle applied thereto. Those skilled in the art will understand that the present disclosure is not limited to the specific embodiments described herein, and various obvious changes, readjustments and substitutions can be made by those skilled in the art without departing from a scope of the present disclosure. Therefore, although the present disclosure has been illustrated in details through the embodiments described above, the present disclosure is not limited to the embodiments described above and may also include many other equivalent embodiments without departing from an inventive concept of the present disclosure, and the scope of the present disclosure is determined by a scope of the appended claims.

What is claimed is:

1. A method for measuring relaxation time of ultrashort echo time magnetic resonance fingerprinting, comprising steps of:

S1, establishing design and implementation of an echo magnetic resonance fingerprint imaging sequence, comprising optimization of sinusoidal fluctuation echo time parameters;

S2, scanning a subject through a magnetic resonance scanner by utilizing the echo magnetic resonance fingerprint imaging sequence established in S1, so as to obtain original k-space data;

S3, reconstructing the original k-space data obtained in S2 into a series of down-sampled images; and S4, phases of the series of down-sampled images in S3 being results of echo time TE of sinusoidal fluctuation modulated with non-uniformity of a B0 field: Phase=2pi·$B_{off}$·($\alpha$ sin($\omega\tau$)+$\beta$)+n, where, $B_{off}$ is a frequency shift caused by field non-uniformity and chemical shift and has a unit of Hz, $\alpha$, $\beta$ and $\omega$ are sampling parameters of the TE, $\alpha$=($TE_{max}$−$TE_{min}$)/2, $\beta$=($TE_{max}$+$TE_{min}$)/2, $TE_{max}$ and $TE_{min}$ are respectively maximum TE and minimum TE; $\omega$ is a frequency of a sinusoidal wave; $\tau$ is a time vector $[1, 2, \ldots, F]^T$, and the time unit is a repetition time TR; n represents a noise term, and demodulation of $B_{off}$ is realized by multiplying a carrier sin($\omega\tau$) followed by low-pass filtering;

S5, moving-averaging a fingerprint signal by sliding window technology, and then performing amplitude demodulation on S4, that is, calculating $B_{off}$:

$$B_{off} = \frac{2}{2\pi \cdot \alpha \cdot mT} \cdot \sum_{0}^{mT} (S \cdot dPhase)$$

by multiplying by the carrier sin($\omega\tau$) followed by low-pass filtering;

where, dPhase is a phase signal multiplied by sin($\omega\tau$) in S4, mT is a phase integral period, m is a number of cycles, $\pi$ is PI, T=$2\pi/\omega$, S is a matrix of F×F, an element contained is either 0 or 1, each row of S represents a window; if and only if the signal is in the window, a value of the element is 1, otherwise the value of the element is 0; and from the first row to the last row in the matrix S, the window moves from left to right;

S6, compensating $B_{off}$ calculated in S5 into the fingerprint signal processed by sliding window; then, reconstructing a multi-parameter quantitative graph from the collected fingerprint signal by a dictionary recognition method in the magnetic resonance fingerprint imaging technology; and S7, according to tissue relaxation time reconstructed in S6, looking up in a dictionary to obtain a corresponding longitudinal magnetization vector change curve, selecting an image with a highest contrast of a bone tissue as a bone enhancement image, which is recorded as Mz, and using Mz/T1 as output of the bone enhancement image, so as to suppress a long T1 tissue, where T1 is a quantitative result of the longitudinal relaxation time outputted in S6.

2. The method for measuring relaxation time of ultrashort echo time magnetic resonance fingerprinting according to claim 1, wherein the optimization of parameters in S1 is implemented by selecting echo time parameters with the highest measurement accuracy by a MATLAB simulation method, and the echo time parameters comprises the minimum echo time, the maximum echo time and a sinusoidal fluctuation period.

3. The method for measuring relaxation time of ultrashort echo time magnetic resonance fingerprinting according to claim 1, wherein in S3, the original k-space data in S2 is reconstructed into the series of down-sampled images by a non-uniform fast Fourier transform reconstruction algorithm.

4. The method for measuring relaxation time of ultrashort echo time magnetic resonance fingerprinting according to claim 1, wherein in S5, when a width of the sliding window is 4, S is written as:

$$S = \begin{pmatrix} 1 & 1 & 1 & 1 & 0 & \ldots & 0 & 0 \\ 0 & 1 & 1 & 1 & 1 & \ldots & 0 & 0 \\ 0 & 0 & 1 & 1 & 1 & \ldots & 0 & 0 \\ & & & \vdots & & & & \\ 0 & 0 & 0 & 0 & 0 & \ldots & 1 & 1 \end{pmatrix}_{F \times F}.$$

* * * * *